United States Patent [19]

Kitano et al.

[11] Patent Number: 5,210,029
[45] Date of Patent: May 11, 1993

[54] METHOD OF PRODUCING INTERLEUKIN-2

[75] Inventors: Kazuaki Kitano, Sakai; Shigeru Fujimoto, Hikari, both of Japan

[73] Assignee: Takeda Chemical Industries, Ltd., Osaka, Japan

[21] Appl. No.: 539,612

[22] Filed: Jun. 18, 1990

Related U.S. Application Data

[63] Continuation of Ser. No. 302,098, Jan. 24, 1989, abandoned, which is a continuation of Ser. No. 185,305, Apr. 20, 1988, abandoned, which is a continuation of Ser. No. 858,454, May 1, 1986, abandoned.

[30] Foreign Application Priority Data

Oct. 3, 1985 [JP] Japan ................................ 60-221517
Mar. 3, 1986 [JP] Japan ................................ 61-45667

[51] Int. Cl.$^5$ .......................... C12P 21/02; C12N 1/38
[52] U.S. Cl. ................................ 435/69.52; 435/69.5; 435/244; 530/351
[58] Field of Search ............... 435/69.5, 69.51, 69.52, 435/244, 240.3, 240.31; 530/351

[56] References Cited

U.S. PATENT DOCUMENTS 4,656,131  4/1987  Kitano et al. .................... 435/68

OTHER PUBLICATIONS

Blohm, et al., (1987) Chem. Abst. 107:174404e.

Primary Examiner—Charles L. Patterson, Jr.
Attorney, Agent, or Firm—Conlin, David G.; Ernest V. Linek

[57] ABSTRACT

The present invention provides an improvement in a method for producing physiologically active proteins by cultivating *Escherichia coli* having an expression vector which contains a structural gene for such proteins at the downstream end of the translational starting codon. The method comprises cultivating the *Escherichia coli* in a medium containing (1) an iron ion source, a manganese ion source or a mixture thereof and (2) a nitrogen source derived from natural origin. The advantage of this method is an increase in the yield of physiologically active proteins substantially free of methionine (corresponding to translational starting codon ATG) at the N-terminus.

15 Claims, 6 Drawing Sheets

Figure 1

```
  1
Ala Pro Thr Ser Ser Thr Lys Lys Thr Gln Leu Gln
                         20
Leu Glu His Leu Leu Leu Asp Leu Gln Met Ile Leu Asn

Gly Ile Asn Asn Tyr Lys Asn Pro Lys Leu Thr Arg Met
 40
Leu Thr Phe Lys Phe Tyr Met Pro Lys Lys Ala Thr Glu
                         60
Leu Lys His Leu Gln Cys Leu Glu Glu Glu Leu Lys Pro

Leu Glu Glu Val Leu Asn Leu Ala Gln Ser Lys Asn Phe
 80
His Leu Arg Pro Arg Asp Leu Ile Ser Asn Ile Asn Val
                             100
Ile Val Leu Glu Leu Lys Gly Ser Glu Thr Thr Phe Met

Cys Glu Tyr Ala Asp Glu Thr Ala Thr Ile Val Glu Phe
         120
Leu Asn Arg Trp Ile Thr Phe Cys Gln Ser Ile Ile Ser
         133
Thr Leu Thr
```

Figure 2

5'GGGGGGGGGGGGGGGGGGATCACTCTCTTTAATCACTACTCACAGTAACC

S1
TCAACTCCTGCCACA ATG TAC AGG ATG CAA CTC CTG TCT TGC

S20 1
ATT GCA CTA AGT CTT GCA CTT GTC ACA AAC AGT GCA CCT

ACT TCA AGT TCT ACA AAG AAA ACA CAG CTA CAA CTG GAG

20
CAT TTA CTG CTG GAT TTA CAG ATG ATT TTG AAT GGA ATT

40
AAT AAT TAC AAG AAT CCC AAA CTC ACC AGG ATG CTC ACA

TTT AAG TTT TAC ATG CCC AAG AAG GCC ACA GAA CTG AAA

60
CAT CTT CAG TGT CTA GAA GAA GAA CTC AAA CCT CTG GAG

80
GAA GTG CTA AAT TTA GCT CAA AGC AAA AAC TTT CAC TTA

AGA CCC AGG GAC TTA ATC AGC AAT ATC AAC GTA ATA GTT

100
CTG GAA CTA AAG GGA TCT GAA ACA ACA TTC ATG TGT GAA

TAT GCT GAT GAG ACA GCA ACC ATT GTA GAA TTT CTG AAC

120
AGA TGG ATT ACC TTT TGT CAA AGC ATC ATC TCA ACA CTG

133
ACT TGA TAATTAAGTGCTTCCCACTTAAAACATATCAGGCCTTCTATTT

ATTTAAATATTTAAATTTTACCCCCCCCCCCCCC3'

Figure 3

```
  1
Cys Asp Leu Pro Gln Thr His Ser Leu Gly Ser Arg Arg
                              20
Thr Leu Met Leu Leu Ala Gln Met Arg Lys Ile Ser Leu

Phe Ser Cys Leu Lys Asp Arg His Asp Phe Gly Phe Pro
 40
Gln Glu Glu Phe Gly Asn Gln Phe Gln Lys Ala Glu Thr
                              60
Ile Pro Val Leu His Glu Met Ile Gln Gln Ile Phe Asn

Leu Phe Ser Thr Lys Asp Ser Ser Ala Ala Trp Asp Glu
     80
Thr Leu Leu Asp Lys Phe Tyr Thr Glu Leu Tyr Gln Gln
                              100
Leu Asn Asp Leu Glu Ala Cys Val Ile Gln Gly Val Gly

Val Thr Glu Thr Pro Leu Met Lys Glu Asp Ser Ile Leu
         120
Ala Val Arg Lys Tyr Phe Gln Arg Ile Thr Leu Tyr Leu
                              140
Lys Glu Lys Lys Tyr Ser Pro Cys Ala Trp Glu Val Val

Arg Ala Glu Ile Met Arg Ser Phe Ser Leu Ser Thr Asn
             160                 165
Leu Gln Glu Ser Leu Arg Ser Lys Glu
```

Figure 4

1
Cys Tyr Cys Gln Asp Pro Tyr Val Lys Glu Ala Glu Asn

20
Leu Lys Lys Tyr Phe Asn Ala Gly His Ser Asp Val Ala

Asp Asn Gly Thr Leu Phe Leu Gly Ile Leu Lys Asn Trp

40
Lys Glu Glu Ser Asp Arg Lys Ile Met Gln Ser Gln Ile

60
Val Ser Phe Tyr Phe Lys Leu Phe Lys Asn Phe Lys Asp

Asp Gln Ser Ile Gln Lys Ser Val Glu Thr Ile Lys Glu

80
Asp Met Asn Val Lys Phe Phe Asn Ser Asn Lys Lys Lys

100
Arg Asp Asp Phe Glu Lys Leu Thr Asn Tyr Ser Val Thr

Asp Leu Asn Val Gln Arg Lys Ala Ile His Glu Leu Ile

120
Gln Val Met Ala Glu Leu Ser Pro Ala Ala Lys Thr Gly

140
Lys Arg Lys Arg Ser Gln Met Leu Phe Arg Gly Arg Arg

146
Ala Ser Gln

METHOD OF PRODUCING INTERLEUKIN-2

CROSS-REFERENCE TO RELATED APPLICATIONS

The present application is a continuation of application Ser. No. 07/302,098, filed Jan. 24, 1989, now abandoned; which in turn is a continuation of application Ser. No. 07/185,305, filed Apr. 20, 1988, now abandoned; which in turn is a continuation of application Ser. No. 06/858,454, filed May 1, 1986, now abandoned.

BACKGROUND OF THE INVENTION

This invention relates to a method for the production of proteins.

The presence of a variety of physiologically active proteins such as cytokines and peptide hormones has been ascertained and recent advances in genetic engineering technology are opening ways for large-scale production of these physiologically active proteins and clinical application of the same.

Interleukin-2 [hereinafter referred to as IL-2; also called T cell growth factor (TCGF)] is a lymphokine produced by T cells upon stimulation by a lectin or alloantigen, among others [Science, 193, 1007 (1976)].

A large number of clones of killer T cells or helper T cells and, further, natural killer cells have so far been obtained through the utilization of IL-2 [e.g. Nature, 268, 154 (1977)]. In addition to such direct use in cloning T cells or natural killer cells, the use of IL-2 can result in selective in vitro proliferation of antigen-specific killer T cells capable of recognizing and destroying a certain particular antigen, for example a tumor antigen By introducing into animals tumor-specific killer T cells grown in this manner, it is possible to control or inhibit tumor growth [The Journal of Immunology, 125, 1904 (1980)].

These experimental findings suggest the possible utility of IL-2 as an antitumor agent It is further known that IL-2 restores the helper T cell function in nude mice which are deficient in thymus function [European Journal of Immunology, 10, 719 (1980)] and restores the induction of killer T cells against allogenic cells [Nature, 284, 278 (1980)], and therefore IL-2 can be expected to be useful in the treatment of immunocompromised diseases Interferon-α (hereinafter referred to as IFN-α) and interferon-γ (hereinafter referred to as IFN-γ) are lymphokines produced by virus- or nucleic acid-activated lymphocytes, are biologically active in that they act on cells and bring them into an antiviral state, and thus play an important role in the prophylactic system or oncoimmune system.

Proteins such as these cytokines can be obtained as naturally occurring substances but in very limited amounts. However, recent advances in recombinant DNA technology have opened the way for the recovery of biologically active proteins from cultures of those strains of Escherichia coli and so forth which respectively carry expression vectors with genes for said proteins inserted therein [for IL-2: Nature, 302, 305 (1983) and Nucleic Acids Research, 11, 4307 (1983); for IFN-α: Journal of Interferon Research, 1, 381 (1981); for IFN-γ: Nature, 295, 503 (1982)].

Since, whether it takes place in a eukaryote or in a prokaryote, protein biosynthesis starts with the messenger RNA codon AUG (which corresponds to methionine,) it is possible that the product protein may possibly be either a molecular species having a methionine residue at the N-terminal end or a molecular species having no such residue or a mixture of the two. In fact, it is known, for instance, that in Escherichia coli, the N-terminal end of many cell proteins is methionine [Conn & Stumpf: Outlines of Biochemistry, 4th edition, John Wiley & Sons (1976)] and that the initiation factor IF-3 of Escherichia coli comprises both the molecular species having a methionine residue at the N-terminal end and the species free of such residue [Hoppe-Seyler's Zeitschrift fur Physiologische Chemie, 354, 1415 (1973)]. With regards to proteins produced in Escherichia coli by using recombinant DNA techniques, it is known that the percentage of a addition of methionine residue to the N-terminal end is about 50% for IFN-α [Journal of Interferon Research, 1, 381 (1981)] and as high as 100% for human growth hormone [Nature, 293, 408 (1981)]. However, no instances have so far been reported to the control of the percentages of methionine residue addition percentage in such proteins In the course of their investigations concerning the process for producing the IL-2 protein using strains of Escherichia coli with the IL-2 gene introduced therein, the present inventors found that the IL-2 protein produced in Escherichia coli is comprised of two molecular species, namely an N-terminal methionine residue-free IL-2, that is a molecular species beginning with an alanine residue as the N-terminal amino acid [Ala-IL-2], and a molecular species having a methionine residue added to the N terminal end and thus beginning with a methionyl-alanine residue [Met-Ala-IL-2], the content of the latter being much higher than that of the former.

Similarly, it was found that when IFN-α and IFN-γ are produced in Escherichia coli each is a mixture of a molecular species the N-terminal end of which begins with a cysteine residue [Cys-IFN-α and Cys-IFN-γ, respectively] and a molecular species having a methionine residue added to the N terminal and thus beginning with a methionyl-cysteine residue [Met-Cys-IFN-α and Met-Cys-IFN-γ, respectively], the latter accounting for from 5-50%.

Those proteins which have a methionine residue at the N-terminal end are supposed to be similar in biological activity to the corresponding proteins of the naturally occurring type but, in any event, are different substances from the latter. Therefore, the known methods are not fully satisfactory for producing proteins having the respective amino acid sequences of the naturally occurring type protein.

SUMMARY OF THE INVENTION

The present invention provides an improvement in the method for producing proteins by cultivating Escherichia coli having an expression vector which contains a structural gene for the protein at the downstream end of translational starting codon, which comprises cultivating the Escherichia coli in a medium containing (1) an iron ion source, a manganese ion source or a mixture thereof and (2) a nitrogen source from natural origin to increase the yield of the protein free of methionine corresponding to translational starting codon ATG at the N-terminus.

As the above-mentioned protein, there may be mentioned a variety of physiologically active proteins, for example cytokines such as interferons (e.g. IFN-α, IFN-β, IFN-γ), interleukins (e.g. interleukin-1, IL-2), B cell growth factor (BGF), B cell differentiation factor (BDF), macrophage activating factor (MAF), lymphotoxin (LT) and tumor necrosis factor (TNF); transforming growth factor (TGF-α); peptide protein hormones such as erythropoietin, epidermal growth factor, insulin and human growth hormone; pathogenic microbial antigen proteins such as hepatitis B virus antigen, influenza virus antigen, foot and mouth disease virus antigen and malarial parasite antigen; enzymes such as peptidases (e.g. tissue plasminogen activator, urokinase, serratiopeptidase) and lysozyme; and serum proteins such as human serum albumin (HSA)

The method of the present invention may be applied with particular advantage to those instances in which IL-2, IFN-α and IFN-γ, among others, are produced by cultivating certain strains of *Escherichia coli.*

The term "IL-2" as used herein refers to any species having the same biological or immunological activities that natural human IL-2 has, for example the IL-2 receptor-binding or anti-IL-2 antibody-binding abilities. Thus, for example, such species may be a polypeptide having the amino acid sequence shown in FIG. 1 [polypeptide (I)] or a fragment thereof comprising some or other part of the amino acid sequence as required for the biological or immunological activities of polypeptide (I), such as a fragment of polypeptide (I) which is lacking one amino acid [EPC (laid open) No. 91539] or 4 amino acids (Japanese Patent Application No. 58-235638, filed on Dec. 13, 1983 and laid open under Japanese Patent Publication No. 126088/1985) from the N-terminal end thereof or a fragment of polypeptide (I) which is lacking in several amino acids of the C terminal portion thereof. Furthermore, such species may be a polypeptide which is otherwise the same as the above polypeptide (I) but is lacking in part of the constituent amino acids of polypeptide (I) or containing one or more amino acids other than the amino acid or acids originally occurring in polypeptide (I), such as a polypeptide (I) analog which contains a serine residue in lieu of the No. 125-cysteine residue [Japanese Patent Publication (laid open) No. 93093/1984]. The polypeptides mentioned above are preferably in the unglycosylated form.

The term "IFN-α" as used herein refers to any species having the same biological or immunological activities that natural human IFN-α has, for example the IFN-α receptor-binding or anti-IFN-α antibody-binding abilities. An example is a polypeptide having the amino acid sequence shown in FIG. 3 [polypeptide (II)]. Furthermore, said species may be a fragment having a partial amino acid sequence exhibiting the biological or immunological activities of IFN-α, such as a fragment of polypeptide (II) which is lacking in several amino acids of the N-terminal portion thereof or in several amino acids of the C-terminal portion thereof. It may further be a polypeptide which is otherwise the same as the above polypeptide (II) but is lacking part of the constituent amino acids of polypeptide (II) or containing one or more amino acids other than the amino acid or acids originally occurring in polypeptide (II). Particularly preferred among them is IFN-αA.

The term "IFN-γ" as used herein refers to any species having the same biological or immunological activities that natural human IFN-γ has, for example the IFN-γ receptor-binding or anti-IFN-γ antibody-binding abilities. Examples are the polypeptide (III) shown in FIG. 4 which comprises 146 amino acids and various fragments of polypeptide (III). Specific examples of such fragments are an N terminal-lacking molecular species which is lacking up to 4 amino acids of the N-terminal portion of polypeptide (III) and a C terminal-lacking molecular species resulting from cleavage of polypeptide (III) or a corresponding N terminal-lacking molecular species at a site not preceding the 131st amino acid residue. Furthermore, the above-mentioned IFN-γ may be an analog thereof which contains a serine or threonine residue in place of the cysteine residue in the above polypeptide. Among others, polypeptide (III) is preferred.

The protein-encoding structural gene may be any DNA, either naturally-derived or synthetic, which codes for the amino acid sequence of the above protein. Thus, for instance, there may be mentioned, for IL-2, a DNA having the base sequence shown in FIG. 2 [DNA (IV)] which codes for the amino acid sequence shown in FIG. 1]; for IFN-α, a DNA [DNA (V); e.g. Japanese Patent Publication (laid open) No. 79897/1982] coding for the amino acid sequence (IFN-αA) shown in FIG. 3; and, for IFN-γ, a DNA [DNA (VI); e.g. Japanese Patent Publication (laid open) No. 189197] coding for the amino acid sequence shown in FIG. 4.

The above-mentioned structural gene (DNA) exists downstream from the translation start codon ATG. Said gene may be present downstream from ATG either in direct connection therewith or via a spacer incapable of being expressed or some other structural gene occurring between ATG and said gene. It is particularly preferable that ATG and the structural gene are directly connected with each other.

It is preferable that the above-mentioned gene (DNA) has a promoter upstream therefrom. Said promoter may be any of the λPL or λPR promoter which takes part in the growth of λ phage, the tryptophan (trp) promoter, the lactose (lac) promoter, the protein chain elongation factor Tu (tuf B) promoter and the rec A promoter, among others. In particular, the λPL and trp promoters may be used in the practice of the present invention with particular advantage.

The above gene and promoter are generally inserted into a vector to yield an expression vector. As the plasmid for producing said a vector, there is used most frequently ColEl-derived pBR322 [Gene, 2, 95 (1977)], for instance, but any other plasmids capable of being maintained by replication in *Escherichia coli* may also be used. Examples are pBR313 [Gene, 2, 75 (1977)], pBR324 and pBR 325 [Gene, 4, 121 (1978)], pBR327 and pBR328 [Gene, 9, 287 (1980)], pKY2289 [Gene, 3, 1(1978)], pKY2700 [Seikagaku (Biochemistry), 52, 770 (1980)], pACYC177 and pACYC184 [Journal of Bacteriology, 134, 1141 (1978)], and pRK248, pRK646 and pDF41 [Methods in Enzymology, 68, 268 (1979)].

Bacteriophage-derived vectors, for example λ phage-derived λgt series vectors such as λgt·λC [Proceedings of the National Academy of Sciences USA, 71, 4579 (1974)], λgt·λB [ibid., 72, 3416 (1975)] and λDam Gene, 1, 255 (1977)], Charon vectors [Science, 196, 161 (1977); Journal of Virology, 29, 555 (1979)], and filamentous phage-derived vectors may also be used as expression vectors.

The above-mentioned expression vector may be constructed by an appropriate known method [e.g. Nature, 302, 305 (1983); Nucleic Acids Research, 11, 4307 (1983); Japanese Patent Publication (laid open) No. 79897/1982; Japanese Patent Publication (laid open) No. 18197/1983].

As the host into which the expression plasmid with a structural gene for a protein inserted therein is to be introduced, a strain of *Escherichia coli* is used and an *Escherichia coli* K-12-derived strain is particularly preferred from handling and safety viewpoints. Examples of said *Escherichia coli* K-12-derived strain which are used with advantage are the strains 294, RR-1, DH-1, N4830 and C-4.

The strain 294 is a known strain [Proceedings of the National Academy of Sciences USA, 73, 4174 (1976)] which has been deposited with the Institute for Fermentation, Osaka (IFO) under the deposit No. IFO-14171.

The strain RR-1 is described in Gene, 2, 75 (1977), the strain DH 1 in Nature, 217, 1110 (1968), and the strain N4830 in Cell, 25, 713 (1981). Having the temperature-sensitive cI represser in the host, the strain N4830 is especially useful when λPL is used as the expression promoter, and it is commercially available from Pharmacia P-L Biochemicals.

The strain C-4 is deposited at IFO under IFO-14421 and at FRI under FERM BP-966, respectively.

The *Escherichia coli* strain to be used in the practice of the present invention may be produced by transforming a host *Escherichia coli* strain with an expression vector containing the structural gene for a protein and the transformation may be effected by the means described, for example, in Journal of Molecular Biology, 53, 159 (1970), Methods in Enzymology, 68 253 (1979), Gene, 3, 279 (1978), and Proceedings of the National Academy of Sciences USA, 69, 2110 (1972).

In accordance with the present invention, the above *Escherichia coli* strain is cultivated in a medium supplemented with an iron ion source and/or a manganese ion source.

Referring to the iron ion source and manganese ion source to be added to the medium, the iron ion source means a substance capable of supplying iron ions when it is dissolved or a substance capable of being utilized in the form of iron ions. Iron salts are examples. Preferred are inorganic salts of divalent or trivalent iron (e.g. ferrous chloride, ferric chloride, ferrous sulfate, ferric sulfate, ferric phosphate, ferric nitrate), among which mineral acid salts of trivalent iron (e.g. ferric chloride, ferric sulfate) are most preferred.

The manganese ion source means a substance capable of yielding manganese ions upon dissolution or a substance capable of being utilized in the form of manganese ions. Examples of such substance are manganese salts, preferably inorganic salts of manganese (e.g. manganese sulfate, manganese chloride, manganese carbonate, manganese phosphate), most preferably mineral acid salts of manganese (e.g. manganese sulfate, manganese chloride).

The iron ion source and manganese ion source may be used either alone or in combination. They are preferably added in the form of aqueous solutions.

The iron ion source and manganese ion source are each added at a concentration of $10^{-6}$ to $10^{-3}$ moles, preferably $2\times10^{-5}$ to $5\times10^{-4}$ moles, per liter. When used in combination, they are added each to a concentration within the above range.

The medium supplemented with nitrogen sources of natural origin which is to be used for cultivating the above *Escherichia coli* strain is a medium prepared by supplementing a known basal medium with a nitrogen source obtained from a naturally occurring substance, such as casamino acids, peptone, yeast extract or malt extract. The nitrogen source is usually supplemented in a concentration from 1 g/l to 50 g/l. A few examples of such medium which are suited for the practice of the present invention are given, in Table 1.

TABLE 1

| Constituent | Examples of medium suited for use | | |
|---|---|---|---|
| | Modified M-9 medium | M-33 medium | M-03 medium |
| Glucose | 10 g/l | 10 g/l | 10 g/l |
| Na$_2$HPO$_4$ | 6 g/l | 3 g/l | — |
| KH$_2$PO$_4$ | 3 g/l | 3 g/l | 3 g/l |
| NaCl | 0.5 g/l | 0.5 g/l | 0.5 g/l |
| NH$_4$Cl | 1 g/l | 1 g/l | 1 g/l |
| MgSO$_4$.7H$_2$O | 0.34 g/l | 0.34 g/l | 0.34 g/l |
| Casamino acids | 10 g/l | 10 g/l | 10 g/l |

The method of the present invention may be conducted under an acidic condition, especially in *Escherichia coli* harboring an expression plasmid and having trp promoter, such that *Escherichia coli* is inoculated into a medium of pH 4.8 to 6.0 and cultured while maintaining the range. A pH range of 5.0 to 5.8 is more recommended; a pH value of approx. 5.5 is particularly conductive to culturing.

After sufficient growth, however, culture conditions may be shifted out of this pH range, e.g. to more acidic conditions.

pH is adjusted using an inorganic base or a mineral acid before or after the medium is prepared and sterilized. pH adjustment may be required during *E. coli* cultivation to maintain the pH within the specified range. Since pH usually decreases during cultivation, pH is adjusted by adding an inorganic base, e.g. ammonia, sodium hydroxide, and sodium carbonate; however, mineral acids such as sulfuric acid may be added, if desired. Of these substances, ammonia water is especially preferable as it constitutes a nitrogen source for the media.

For transformants harboring an expression plasmid and having a trp promoter, for instance, an agent for causing the promoter to function efficiently, for example 3-β-indolylacrylic acid, may be added.

In case the host is an auxotroph, the amino acid or amino acids required (e.g. L-lysine, L-arginine, L-methionine, L-leucine, L-proline, L-isoleucine, L-valine, L-tryptophan) are preferably each added to a concentration of about 10 to 1,000 mg/liter. It is also possible to additionally supplement glucose, casamino acids and other components during cultivation as necessary. Furthermore, for selective growth of the recombinant *Escherichia coli* strain, an agent to which the strain is resistant, for example tetracycline, may be added, depending on the gene for drug resistance or the like retained in the plasmid.

The medium used for large scale cultivation is prepared in advance (namely, before starting fermentation) by adding the iron ion source and/or manganese ion source (mentioned above) at an appropriate concentration. seed culture medium.

The cultivation is generally carried out at 15°-45° C. In strains carrying the λPR or λPL promoter and the temperature sensitive repressor, for instance, proliferation at 25°-35° C. followed by shifting up to about 42° C. is advantageous for gene expression. In strains carrying other promoters, high productivity may be attained by maintaining a temperature of about 37° C. from the beginning of growth to about the middle thereof and then decreasing the temperature with proliferation, followed by maintenance at 20°-30° C.

The cultivation is generally performed with aeration and stirring. Cultivation while maintaining the oxygen concentration in medium at a level of not lower than about 5% (v/v) of the saturation oxygen concentration is advantageous since, in that case, an increased yield of the desired protein may be obtained.

The protein thus produced may be assayed by a known method.

For assaying IL-2, for instance, an IL-2-dependent cell line may be used. Since human IL-2 is known to promote the growth of rat, mouse and some other IL-2-dependent cell lines as well as human cell lines [Immunological Reviews, 51, 257 (1980)], not only human IL-2-dependent cell lines but also rat or mouse IL-2-dependent cell lines may be used [Journal of Immunology, 130, 981 and 988 (1983)].

In particular, IL-2-dependent murine cell lines may be stably maintained by passage for a long period of time and give assay results with high reproducibility.

The total IL-2 yield data given in this specification are data as measured by the method which uses IL-2-dependent cells and takes the uptake of radioactive thymidine as an index [Biochemical and Biophysical Research Communications, 109, 363 (1982)].

The yield of Ala-IL-2 was determined by extracting IL-2 from cells with 7M guanidine hydrochloride, dialyzing the extract, subjecting the dialyzate to FPLC (fast protein liquid chromatography) to be mentioned later herein for separation of an Ala-IL-2 fraction and a Met-Ala-IL-2 fraction, determining IL-2 activities of both fractions by the method mentioned above, calculating the proportion of Ala-IL-2 and multiplying the total yield of IL-2 by this proportion.

Purified samples (i.e., an Ala-Il-2 fraction and a Met-Ala-Il-2 fraction), which were obtained by FPLC, were quantified by measuring the absorbance values at 280 nm, respectively and the proportion of Ala-Il-2 was calculated from the measured values.

IFNs are assayed either by the antiviral assay method [Journal of Virology, 37, 755 (1981)] or by the enzyme immunoassay method [Journal of Immunology, 80, 55 (1985)]. The proportion of the IFN species having N-terminal methionine relative to the whole IFN produced is determined by subjecting the IFN protein extracted from cells and purified by appropriate methods, for examples a purified sample of IFN-αA, to FPLC to thereby separate the molecular species having N-terminal methionine and the molecular species without N-terminal methionine, which are quantified by measuring an absorbance value at 280 nm, respectively and the proportion of the species having N-terminal methionine relative to the whole IFN produced is then calculated based on the measured values. In the case of IFN-γ, both species are quantified by determining the N-terminal methionine content by the dansylation method or by using a peptide sequenser.

In extracting the protein produced in accordance with the present invention from cultured cells, the cells are harvested after cultivation and suspended in a buffer containing a protein-denaturing agent such as guanidine hydrochloride and, after stirring in a cool place, a supernatant containing the protein is collected by centrifugation. In accordance with another method, cells are suspended in a buffer and disrupted by sonication, lysozyme treatment and/or freezing and thawing, and then a supernatant containing the protein is collected by centrifugation. Any other appropriate methods may also be used.

The protein may be isolated from the above-mentioned supernatant and purified by an appropriate combination of per se known methods of separation and purification. Examples of such known separation and purification methods are methods making good use of solubility differences, such as salting out and solvent precipitation; methods mainly utilizing molecular weight differences, such as dialysis, ultrafiltration, gel filtration and SDS-polyacrylamide gel electrophoresis; methods making use of electric charge differences, such as ion exchange chromatography; methods based on specific affinity, such as affinity chromatography; methods based on hydrophobicity differences, such as reversed-phase high-performance liquid chromatography; and methods utilizing isoelectric point differences, such as isoelectric focusing In particular, the human IL-2 protein, which has high hydrophobicity, may be purified very effectively by hydrophobic column chromatography, in particular by high-performance liquid chromatography using a reversed-phase type column. For IFN-α and IFN-γ, the method of purification which uses monoclonal antibodies capable of specifically binding to the respective IFN species is very effective.

When the above IL-2 protein is a mixture of Ala-IL-2 and Met-Ala-IL-2, Ala-IL-2 may be isolated, as desired, by the separation means based on isoelectric point differences as disclosed by the same applicant as in the instant application of PCT/JP84/00460 (date of international application: Sep. 26, 1984), for instance.

As the separation means based on isoelectric point differences, there may be used any method of separating proteins differing in isoelectric point by about 0.01–0.2 from one another, for example density gradient isoelectric focusing using Ampholines, gel isoelectric focusing, constant-rate electrophoresis or the like method of electrophoresing proteins in an electric field, chromatofocusing, FPLC (fast protein liquid chromatography), pH gradient DEAE (diethylaminoethyl)- and CM (carboxymethyl) ion exchange column chromatography or the like method of eluting proteins one by one from a column in which a pH gradient is produced, or some other per se known method, or a combination of these. The reagents and apparatus to be used in these methods of separation are all commercially available and may be readily purchased.

A mixture of Cys-INF-α and Met-Cys-IFN-α may also be treated, if desired, in the same manner for mutual separation of the components.

The thus-purified proteins free of the N-terminal methionine residue corresponding to the translation start codon ATG have the same physiological activities as the corresponding known proteins, such as the corresponding naturally occurring proteins, and may be used as pharmaceuticals.

The Ala-IL-2 protein, like known IL-2 species, may cause selective in vitro growth of antigen-specific killer T cells capable of recognizing and destroying tumor antigens, for instance, or of natural killer cells capable of killing tumors. In other words, these cells are lymphocytes which destroy tumor cells and virus infected cells unspecifically, without depending on an immune response which starts with antigen sensitization. Since simultaneous inoculation with said IL-2 with introduction of the above killer cells into a living organism results in an increased antitumor activity of the killer cells, said protein may be used in the prevention and treatment of tumors or in the treatment of immunocompromised diseases in warm-blooded animals (e.g. mouse, rat, rabbit, dog, cat, pig, horse, sheep, cattle, human).

For using the above Ala-IL-2 protein as a prophylactic or therapeutic agent against tumors, said protein may be administered either parenterally or orally in the form of injections or capsules, for instance, as prepared by dilution with a per se known carrier. Furthermore, it may be used either alone or in combination with killer T cells or natural killer cells grown in vitro as mentioned above.

The above-mentioned Ala-IL-2 protein has substantially the same biological activities as known human IL-2 isolated from nature and therefore may be used in the same manner as the latter. Since the constant for its dissociation from cellular IL-2 receptors is very small, administration of said protein in very small doses is sufficient.

IFN, which has antiviral, antitumor, cell proliferation inhibiting, immunopotentiating and other activities, may be used in the treatment of viral infections and tumors, among others, in mammals (e.g. human, cattle, horse, pig, mouse, rat). In using said IFN as an antiviral, antitumor, cell proliferation inhibiting or immunopotentiating agent, for instance, said IFN is mixed with a pharmacologically acceptable carrier, excipient or diluent, which is known per se, and is administered in a form suitable for injections (parenterally intravenously, or intramuscularly, injection, for instance. In normal humans, the daily dose ranges from about 100 thousand to 100 million units, preferably from about 1 million to 50 million units. In mammals other than human, the dose ranges 2,000 to 2 million units/kg/day, preferably from about 20 thousand to 1 million units/kg/day.

BRIEF DESCRIPTION OF THE DRAWINGS

FIG. 1 shows the amino acid sequence of human IL-2.

FIG. 2 shows an example of the DNA base sequence coding for human IL-2.

FIG. 3 shows the amino acid sequence of human IFN-αA.

FIG. 4 shows the amino acid sequence of human IFN-γ.

EXAMPLES

DETAILED DESCRIPTION OF THE PREFERRED EMBODIMENTS

Figure 5:
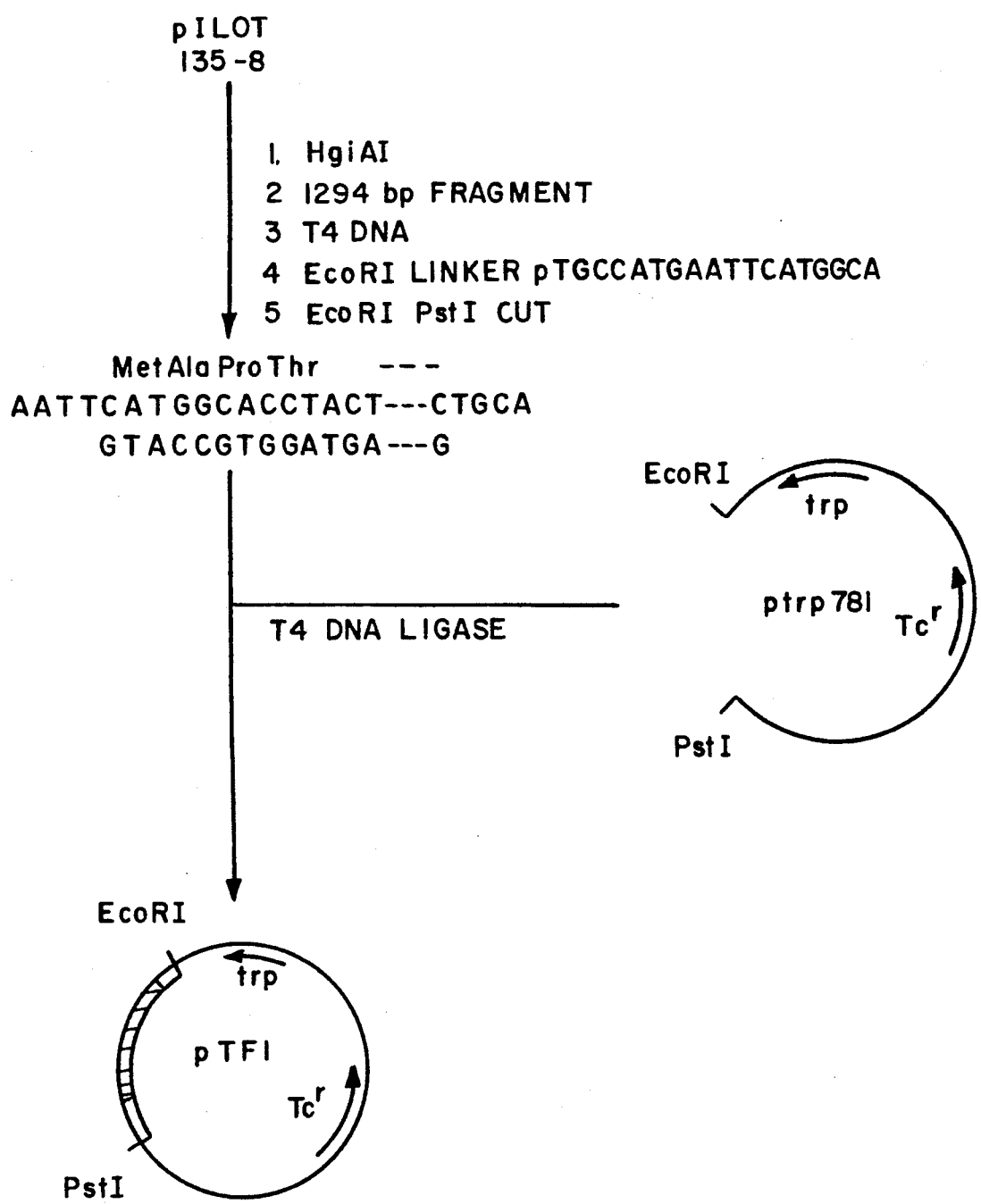
FIG. 5 and FIG. 6 show the schemes for constructing the plasmids pTF1 and pTB285 described in the Reference Example, respectively.

The following examples and reference examples illustrate the present invention in further detail The transformants disclosed in the examples have been deposited with the Fermentation Research Institute (FRI), Agency of Industrial Science and Technology, Ministry of International Trade and Industry and the Institute for Fermentation, Osaka (IFO) under the deposit numbers specified in Table 2.

TABLE 2

| Transformant | Deposited with | |
|---|---|---|
| | FRI (Date of deposition) | IFO |
| Escherichia coli N4830/pTB285 | FERM BP-852 (Apr. 30, 1985) | IFO-14437 |
| Escherichia coli DH1/pTF4 | FERM BP-628 (Apr. 6, 1984) | IFO-14299 |
| Escherichia coli C-4/pTF4 | FERM BP-967 (Feb. 16, 1985) | IFO-14422 |

EXAMPLE 1

A 50-ml portion of a medium prepared by adding 50 mg/liter of sodium ampicillin and 15 mg/liter of tetracycline hydrochloride to L medium (10 g/liter Bacto-tryptone, 5 g/liter Bacto-yeast extract, 5 g/liter sodium chloride) was inoculated with Escherichia coli N4830/pTB285 obtained in Reference Example 1 (ii), followed by overnight incubation at 37° C. with rotation and shaking. The culture broth was transferred to a 5-liter jar fermenter containing 2.5 liters of modified M-9 medium supplemented with one or more metal salts as specifically given in Table 3, and cultivation was started at a rate of aeration of 2.5 liters/minute, a rate of stirring of 1,000 rpm and a temperature of 30° C. In the middle of cultivation, when the growth reached 1,000 Klett units, the temperature was shifted up to 42° C. and, after 4 hours of continued incubation, cells were harvested and frozen. For each culture broth, the frozen cells were examined for Ala-IL-2 productivity. The results obtained were as shown in Table 3.

TABLE 3

| Effects of addition of various metal ions | | | | | | Ala-IL-2 productivity[*2] |
|---|---|---|---|---|---|---|
| Metal ion added[*1] (moles) | | | | | | |
| $Mn^{++}$ | $Fe^{+++}$ | $Cu^{++}$ | $Zn^{++}$ | $Ca^{++}$ | $Co^{++}$ | |
| 0 | 0 | 0 | 0 | 0 | 0 | 100 |
| $4 \times 10^{-5}$ | $4 \times 10^{-4}$ | $2 \times 10^{-5}$ | $3 \times 10^{-5}$ | $7 \times 10^{-5}$ | $2 \times 10^{-5}$ | 500 |
| $4 \times 10^{-5}$ | 0 | 0 | 0 | 0 | 0 | 470 |
| 0 | $4 \times 10^{-4}$ | 0 | 0 | 0 | 0 | 320 |
| $4 \times 10^{-5}$ | $4 \times 10^{-4}$ | 0 | 0 | 0 | 0 | 570 |

[*1] The metal ions were added in the form of the following compounds, respectively: $MnSO_4 \cdot 4-6H_2O$, $FeCl_3 \cdot 6H_2O$, $CuSO_4 \cdot 5H_2O$, $ZnSO_4 \cdot 7H_2O$, $CaCl_2 \cdot 2H_2O$, and $CoCl_2 \cdot 6H_2O$.
[*2] Given in terms of relative value, the productivity for the no metal ion addition case, was assigned a value 100.

As is evident from Table 3, the addition of $Mn^{++}$ and/or $Fe^{+++}$ resulted in an markedly increased Ala-IL-2 productivity whereas the addition of other ion sources ($Cu^{++}$, $Zn^{++}$, $Ca^{++}$, $Co^{++}$) did not improve the productivity to any further extent.

EXAMPLE 2

The Escherichia coli N4830/pTB285 strain was grown in the same manner as in Example 1 in M-33 medium supplemented with the Mn ion in different concentrations, and the results as shown in Table 4 were obtained.

TABLE 4

| Effects of addition of manganese ion | |
|---|---|
| $MnSO_4 \cdot 4-6H_2O$ (moles) | Ala-IL-2 productivity* |
| 0 | 100 |
| $2 \times 10^{-5}$ | 310 |
| $4 \times 10^{-5}$ | 490 |

TABLE 4-continued

Effects of addition of manganese ion

| MnSO$_4$.4-6H$_2$O (moles) | Ala-IL-2 productivity* |
|---|---|
| 8 × 10$^{-5}$ | 600 |
| 2 × 10$^{-4}$ | 360 |

*The productivity for the medium without metal salt addition assigned a value of 100.

EXAMPLE 3

The *Escherichia coli* N4830/pTB285 strain was cultivated in the same manner as in Example 1 in M-33 medium supplemented with the Fe ion in different concentrations, and the results shown in Table 5 were obtained.

TABLE 5

| Effects of addition of iron ion | |
|---|---|
| FeCl$_3$.6H$_2$O (moles) | Ala-IL-2 productivity* |
| 0 | 100 |
| 7 × 10$^{-5}$ | 370 |
| 4 × 10$^{-4}$ | 410 |

*The productivity for the medium without metal salt addition was assigned a value of 100.

EXAMPLE 4

A 50 ml-portion of a liquid medium (pH 7.0) prepared by adding 7 mg/liter of tetracycline hydrochloride to L medium was inoculated with the transformant *Escherichia coli* DH1/pTF4 [Japanese Patent Application No. 225079/1983 filed on Nov. 28, 1983 and laid open under Japanese Patent Publication No. 115528/1985; Example 3], followed by overnight cultivation at 37° C. with rotation and shaking. The culture broth was inoculated into a 5-liter jar fermenter containing 2.5 liters of modified M-9 medium or of the same medium supplemented with 4×10$^{-4}$ moles of FeCl$_3$·6H$_2$O and 4×10$^{-5}$ moles of MnSO$_4$·4—6H$_2$O, and cultivation was started at an aeration rate of 2.5 liters/minute, a stirring rate of 1,000 rpm and a temperature of 37° C. During the cultivation, when the growth reached about 500 Klett units, the temperature was reduced to 30° C. and, when the growth reached about 1,000 Klett units, to 25° C. After 24 hours of cultivation, cells were harvested and frozen, and examined for Ala-IL-2 productivity by extracting IL-2 from the cells The results obtained were as shown in Table 6.

TABLE 6

| Metal ion (moles) | | Ala-IL-2 productivity* |
|---|---|---|
| Mn$^{++}$ | Fe$^{+++}$ | |
| 0 | 0 | 100 |
| 4 × 10$^{-5}$ | 4 × 10$^{-4}$ | 230 |

*The productivity for the medium without metal salt addition was assigned a value of 100.

EXAMPLE 5

Six 50-ml portions of a liquid medium (pH 6.0), which was L medium containing 50 mg/liter of sodium ampicillin, each in a 250-ml erlenmeyer flask was inoculated with *Escherichia coli* N4830/pTB285, followed by overnight cultivation at 30° C. with rotation and shaking. The culture broth was inoculated, in 125-ml portions, into a 2.5-liter portion of M-33 medium containing 50 mg/liter of sodium ampicillin [medium (A)] and a 2.5-liter portion of M-33 medium containing 50 mg/liter of sodium ampicillin, 8×10$^{-5}$ moles of MnSO$_4$·4—6H$_2$O and 4×10$^{-4}$ moles of FeCl$_3$·6H$_2$O medium (B)], and cultivation was started at an aeration rate of 2.5 liters/minute, a stirring rate of 1,000 rpm and a temperature of 30° C., the pH being maintained at 6.5 throughout cultivation with aqueous ammonia. Each time when the glucose concentration decreased to 0.5% (w/v) or below, glucose and casamino acids were added each in an amount corresponding to 1%. Furthermore, when the growth reached 1,000 Klett units, the temperature was raised to 42° C. Four (4) hours after the change in the temperature to 42° C., the cultivation was complete. The culture broth was centrifuged, the cells were harvested, then frozen at −80° C., and stored.

A 12-g portion of the frozen cells from either culture broth was suspended homogeneously in 100 ml of an extractant (pH 7.0) containing 7M guanidine hydrochloride and 0.1M Tris-HCl buffer. After stirring at 4° C. for 1 hour, the suspension was centrifuged at 28,000×g for 20 minutes to give a supernatant.

Each supernatant obtained was dialyzed against 0.01M Tris-HCl buffer (pH 8.5) and centrifuged at 19,000×g for 10 minutes. The supernatant obtained was passed through a DE52 (DEAE-cellulose, Whatman, Great Britain) column (50 ml in volume) equilibrated with 0.01M Tris-HCl buffer (pH 8.5) for effecting protein adsorption. By constructing a linear NaCl concentration gradient (0 to 0.15M NaCl, 1 liter), IL-2 was eluted to give active fractions.

Each active fraction obtained in the above was concentrated to about 5 ml using a YM-5 membrane (Amicon, USA) and the concentrate was subjected to gel filtration using a Sephacryl S-200 (Pharmacia, Sweden) column (500 ml in volume) equilibrated with 0.1M Tris-HCl (pH 8.0)-1M NaCl buffer. Each active fraction measuring about 30 ml was concentrated to about 2.5 ml using a YM-5 membrane. The concentrate was applied to an Ultrapore RPSC (Altex, USA) column for adsorption, followed by high-performance liquid chromatography using a trifluoroacetic acid-acetonitrile system as the eluent. Column, Ultrapore RPSC (4.6×75 mm); column temperature, 30° C.; eluent A, 0.1% trifluoroacetic acid-99.9% water; eluent B, 0.1% trifluoroacetic acid-99.9% acetonitrile; elution program, minute 0 (68% A+32% B)-minute 25 (55% A+45% B)-minute 35 (45% A+55% B)-minute 45 (30% A+70% B)-minute 48 (100% B); elution rate, 0.8 ml/minute; detection wavelength, 230 nm.

For each culture, about 10 ml of an active fraction eluting after about 39 minutes of retention under the above conditions was collected.

Each of the thus-obtained liquids containing a mixture of Ala-IL-2 and Met-Ala-IL-2 was lyophilized and the lyophilizate was dissolved in 5 ml of 0.005M ammonium acetate buffer (pH 5.0) and applied to a Mono P column for FPLC (0.5×20 cm, Pharmacia) equilibrated with 0.025M diethanolamine hydrochloride buffer (pH 9.4) and then the protein adsorbed on the Mono P column was eluted with 1% (v/v) Pharmalite (8–10.5)-5.2% (v/v) Polybuffer 96 hydrochloride buffer (pH 8.0). FPLC was conducted at room temperature and at a flow rate of 30 ml/hour. For each culture, an active eluate fraction of from 17 ml to 19 ml was collected and subjected to high-performance liquid chromatography using a trifluoroacetic acid-acetonitrile system as the eluent for removing Polybuffer. Column, Ultrapore RPSC (1.0×25 cm, Altex); column temperature, eluent A and eluent B, the same as above; elution program, minute 0 (55% A+45% B)-minute 4 (55% A+45%

B)-minute 28 (42% A+58% B)-minute 38 (34% A+66% B)-minute 43 (20% A+80% B)-minute 44 (55% A+45% B); elution rate, 3.0 ml/minute.

Each Ala-IL-2 fraction thus obtained was lyophilized to give a white powder.

The powder mentioned above as obtained from medium (A) without addition of any metal salts weighed 1.53 mg, whereas medium (B) with metal salt addition gave 6.31 mg of a powder.

With these two samples, the N-terminal amino acid was identified by the automatic Edman degradation method using a vapor phase protein sequencer (Applied Biosystems model 470A) and it was confirmed that Ala accounted for 98% or more. It was simultaneously confirmed that other protein chemistry characteristics (C-terminal amino acid, amino acid composition analysis, peptide mapping) of the two samples were quite identical.

EXAMPLE 6

The *Escherichia coli* 294 (ATCC 31446)/pLeIF-A-trp25 strain [cf. Example 1 of EPC (laid open) No. 43980] carrying an expression plasmid with a human IFN-αA gene coding for the amino acid sequence shown in FIG. 3 inserted therein was inoculated into 50 ml of a medium prepared by adding 5 mg/liter of tetracycline hydrochloride to L medium, followed by overnight incubation at 37° C. with rotation and shaking. The culture broth was transferred to a 5-liter jar fermenter containing 2.5 liters of modified M-9 medium supplemented with one or two metal salts specified in Table 7. Cultivation was started at an aeration rate of 2.5 liters/minute, a stirring rate of 1,000 rpm and a temperature of 37° C. The temperature was lowered to 30° C. at an extent of growth of 500 Klett units and further to 25° C. at 1,000 Klett units. Cultivation was performed for 24 hours in that manner. During cultivation, each time the glucose concentration fell to 0.2% (w/v) or below, glucose was added, to give a final concentration of 1% (w/v). each culture broth was centrifuged, whereby cells were harvested, which were suspended in 100 ml 50 mM Tris-HCl (pH 7.6) containing 10% (w/v) sucrose, 0.2M NaCl, 10 mM ethylenediaminetetraacetate (EDTA), 10 mM spermidine, 2 mM phenylmethylsulfonyl fluoride (PMSF) and 0.2 mg/ml lysozyme. After stirring at 4° C. for 1 hour, the suspension was warmed at 37° C. for 5 minutes and, then, further treated in a sonicator (Altex, USA) at 0° C. for 40 seconds. The resulting lysate was centrifuged at 11,300×g for 1 hour to give 95 ml of a supernatant.

This supernatant (95 ml) was diluted with 300 ml of 20 mM Tris-HCl (pH 7.6) containing 1 mM EDTA and 0.15M NaCl (TEN) and the dilution was applied to an anti-IFN-αA antibody column (20 ml).

After washing the column sufficiently with TEN, IFN-αA was eluted with 0.2M acetic acid containing 0.1% Tween 20 (Wako Pure Chemical Industries), the active fraction collected was adjusted to pH 4.5 and applied to a CM cellulose column for adsorption. After sufficient washing of the column, elution was effected with 0.025M ammonium acetate buffer (pH 5.0) containing 0.15M NaCl. The active fraction thus collected again was lyophilized to give a human leucocyte IFN-αA powder in an amount given in the table below.

Each sample thus obtained gave a single band in SDS-polyacrylamide gel electrophoresis and had a molecular weight of 19,000±1,000 and an antiviral activity of 2 to 3×10⁸ U/mg. The sample obtained was subjected to FPLC using a Mono P column for chromatofocusing with Polybuffer from pH 6.7 to pH 5.5, whereby the proportions of the molecular species having an N-terminal methionine and the molecular species free of such methionine were determined. The results were as shown in Table 7. Thus, the addition of manganese and/or iron ions resulted in production of IFN-αA substantially free of the N-terminal methionine-containing molecular species.

TABLE 7

| Metal ion added (moles) | | IFN-αA powder yield (mg) | Proportion of N-terminal methionine-containing species |
|---|---|---|---|
| Mn⁺⁺ | Fe⁺⁺⁺ | | |
| 0 | 0 | 28 | 14.6% |
| 4 × 10⁻⁵ | 0 | 29 | 0.8% |
| 0 | 7 × 10⁻⁵ | 30 | 1.0% |
| 4 × 10⁻⁵ | 7 × 10⁻⁵ | 32 | less than 0.5% |

EXAMPLE 7

*Escherichia coli* RR-1 (pRK248cIts, pRC231/IFN-900) bearing an expression plasmid with a human IFN-γ gene coding for the amino acid sequence shown in FIG. 4 inserted therein as described in Example 8 of Japanese Patent Publication (laid open) No. 189197/1983 was inoculated into 50 ml of a medium prepared by adding 50 mg/liter of sodium ampicillin and 10 mg/liter of tetracycline hydrochloride, followed by overnight incubation at 30° C. with rotation. The culture broth was transferred to a 5-liter jar fermenter containing 2.5 liters of M-33 medium supplemented with one or two metal salts specified in Table 8. Cultivation was started at an aeration rate of 2.5 liters/minute, a starting rate of 1,000 rpm and a temperature of 30° C. At the logarithmic stage, when the growth was at about 700 Klett units, glucose and casamino acids were added each in an amount corresponding to a concentration of 1% (w/v) and at the same time the incubation temperature was raised from 30° C. to 42° C., followed by 4 hours of continued cultivation. Each time when the glucose concentration had become 0.2% or below, glucose and casamino acids were added, each in an amount corresponding to a concentration of 1% (w/v).

After completion of cultivation, the culture broth was centrifuged, whereby cells were collected, which were then frozen and stored.

Extraction of a 100-g portion of frozen cells from each culture with 300 ml of 100 mM Tris-hydrochloride buffer (pH 7.0) containing 7M guanidine hydrochloride was followed by centrifugation, giving a supernatant. This supernatant was diluted 70-fold with a buffer (hereinafter referred to as P.B.S.) comprising 137 mM sodium chloride, 27 mM potassium chloride, 8 mM disodium phosphate and 147 mM monopotassium phosphate and the dilution was again centrifuged to give a clear and transparent supernatant. This supernatant was applied to a monoclonal antibody (γ2-11.1 MoAb; Japanese Patent Publication (laid open) No. 80646/1984) column (50 ml) and, after sufficient washing, elution was carried out with 20 mM phosphate buffer (pH 7.0) containing 2M guanidine hydrochloride. An active fraction was collected and further applied to a Sephacryl S-200 (Pharmacia) column and then to a Sephadex G-25 column, the active fraction was collected in each case, whereby a purified IFN-γ sample was obtained. The yields from the respective media are shown in Table 8.

Each sample obtained showed an IFN-γ purity of not less than 95% and an antiviral activity of 3 to $4\times10^6$ IU/mg. The sample was dansylated and dansyl methionine was isolated and quantified by HPLC. The proportion of the molecular species containing N-terminal methionine relative to the total molecular species was thus determined and the data obtained are shown in Table 8.

TABLE 8

| Metal ion added (moles) | | IFN-yield | Proportion of N-terminal methionine-containing |
|---|---|---|---|
| $Mn^{++}$ | $Fe^{+++}$ | (mg) | molecular species |
| 0 | 0 | 15 | 12.0% |
| $4\times10^{-5}$ | 0 | 16 | 1.0% |
| 0 | $7\times10^{-5}$ | 16 | 1.2% |
| $4\times10^{-5}$ | $7\times10^{-5}$ | 17 | less than 1% |

Thus, the addition of iron and manganese ions resulted in successful production of IFN-γ substantially free of the accompanying, N-terminal methionine-containing molecular species.

EXAMPLE 8

A medium prepared by adding 5 mg/l of tetracycline hydrochloride to L medium was inoculated with *Escherichia coli* C-4/pTF4 obtained in Reference Example 2, followed by cultivation at 37° C. with rotation and shaking (200 rpm) for 16.5 hours. The following media were prepared; (1) an M-03 medium adjusted to pH 5.5 and (2) an M-03 medium supplemented with 20 mg/l of $FeCl_2\cdot6H_2O$ and 10 mg/l of $MnSO_4\cdot6H_2O$. A 2.5 liter portion each of medium (1) and medium (2) were respectively transferred to two 5-liter jar fermenters, and then a 125 ml-portion of the culture broth was inoculated into each of the respective 2.5 liter broths. These media were cultivated at 34.5° C. with 2.5 l/min. aeration stirring with maintaining the pH at 5.5 by the use of 14% aqueous ammonia and 5N sulfuric acid. During the cultivations, when the growth reached about 500 Klett units, the temperature was reduced to 27.5° C., and when the growth reached about 1,000 Klett units, the temperature was lowered to 22.5° C. Six (6) hours after the cultivation was started, 2 g/l of glucose and 2 g/l of casamino acid were added. After 24 hours of cultivation, the culture broths were examined for the production of Ala-IL-2, providing the data shown in Table 9.

Cells were harvested from the culture broth and IL-2 was extracted from the respective 12 g of frozen cells and purified to Ala-IL-2 by the same manner described in Example 5. 2.1 mg and 10.0 mg of Ala-IL-2 were obtained from the cells grown in medium (1) and in medium (2), respectively.

TABLE 9

| Metal salts | | Ala-IL-2 productivity |
|---|---|---|
| — | | 100 |
| $FeCl_3.6H_2O$ | 20 mg/l | |
| $MnSO_4.4–6H_2O$ | 10 mg/l | 509 |

REFERENCE EXAMPLE 1

Production of human IL-2-producing transformant (I)

(i) The human IL-2 gene-containing plasmid pI-LOT135-8 [Japanese Patent Application No. 225079/1983, filed on Nov. 28, 1983 and laid open under Japanese Patent Publication No. 115528/1985; see Example I (vii) thereof] was cleaved with the restriction enzyme HgiAI The 1294 bp DNA fragment obtained was rendered blunt-ended with T4 DNA polymerase and ligated with the EcoRI linker dTGCCAT-GAATTCATGGCA using T4 DNA ligase. The DNA obtained was digested with EcoRI to give a DNA fragment having the translation start codon ATG and the human IL-2 gene.

This DNA fragment was inserted into the plasmid ptrp781 [Nucleic Acids Research, 11, 3077 (1983)] digested in advance at the EcoRI-PstI sites, using T4 DNA ligase. The thus-obtained expression plasmid pTF1 has the translation start codon and human IL-2 gene downstream from the trp promoter (FIG. 5).

Figure 6:
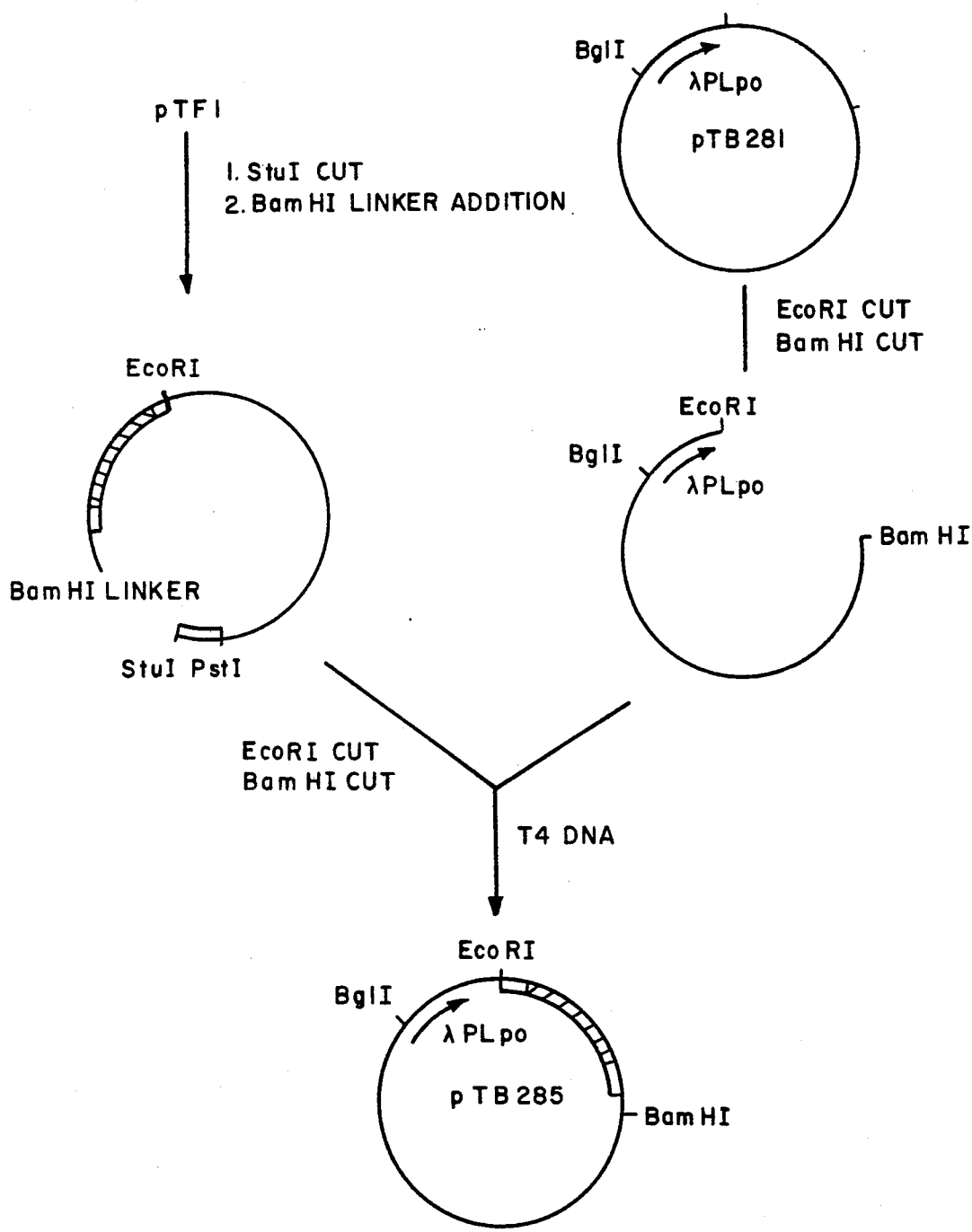

The plasmid pTF1 was cleaved with the restriction enzyme StuI, followed by ligation with the BamHI linker. The resulting plasmid DNA was treated with the restriction enzymes BamHI and EcoRI and the EcoRI-BamHI fragment was inserted into the λPL promoter-containing plasmid pTB281. The thus-obtained expression plasmid was named pTB285 (FIG. 6).

(ii) *Escherichia coli* N4830 was transformed with the plasmid pTB285 obtained in the above by the method of Cohen et al. [Proceedings of the National Academy of Sciences USA, 69, 2110 (1972)], whereby a transformant, *Escherichia coli* N4830/pTB285, was obtained.

REFERENCE EXAMPLE 2

Production of human IL-2-producing transformant (II)

Expression plasmid pTF4, which contains a human IL-2 structural gene, was isolated from *E. coli* DH1/pTF4 [European Patent Publication (laid open) No. 145390] in accordance with the method of Birnboim, H. C. et al. [Nucleic Acids Research, 7, 1513 (1979)]. Using said plasmid, *E. coli* PR 13 [J. Bacterogy, 97, 1522 (1969)] was transformed in accordance with the method of Cohen, S. N. et al. [Proceedings of the National Academy of Science, USA, 69, 2110 (1972)]. The resulting transformant cells were inoculated into media (50 ml, pH 7.0) containing 1% Bacto-trypton (Difco Laboratories, USA), 0.5% Bacto-yeast Extract (same as above), 0.5% sodium chloride and 5 mg/l tetracycline hydrochloride in a conical flask of 200 ml capacity, and then cultured at 37° C. for one night. Each resulting culture liquid was then inoculated into a 200 ml conical flask which has a hollow containing a medium (30 ml) prepared by adding 1 mg/l vitamin $B_1$ hydrochloride to an modified M-9 medium, after which it was continuously cultured at 37° C. for 4 hours, at 30° C. for 4 hours and at 25° C. for 10 hours; a strain possessing an eminently high IL-2 producibility, i.e. *E. coli* C-4/pTF4, was selected.

What is claimed is:

1. In a method for producing the physiologically active protein interleukin-2 by cultivating *Escherichia coli* having an expression vector which contains the structural gene for the protein at the downstream end of a translational starting codon, the improvement comprising cultivating the *Escherichia coli* in a medium to which is added:
   (1) an iron ion source, a manganese ion source, or a mixture thereof, at a concentration of from about $1\times10^{-6}$ to about $1\times10^{-3}$ moles per liter; and
   (2) a nitrogen source derived from natural original at a concentration of from about 1 gram per liter to about 50 grams per liter;
to increase the yield of the protein, free of methionine corresponding to a translational starting codon ATG at the N-terminus.

2. The method according to claim 1, wherein the medium contains an iron ion source at a concentration range of from about $2 \times 10^{-5}$ to about $5 \times 10^{-4}$ moles per liter.

3. The method according to claim 1, wherein the medium contains a manganese iron source at a concentration range of from about $2 \times 10^{-5}$ to about $5 \times 10^{-4}$ moles per liter.

4. The method according to claim 1, wherein the medium contains a mixture of an iron ion source and a manganese ion source, at a total concentration range of from about $2 \times 10^{-5}$ to about $5 \times 10^{-4}$ moles per liter.

5. The method according to claim 1, wherein the expression vector further comprises a promoter.

6. The method according to claim 5, wherein the promoter comprises a $\lambda$PL promoter.

7. The method according to claim 5, wherein the promoter comprises a tryptophan promoter.

8. The method according to claim 1, wherein the iron ion source comprises an inorganic iron salt.

9. The method according to claim 8, wherein the inorganic iron salt comprises a mineral acid salt of trivalent iron.

10. The method according to claim 1, wherein the manganese ion source comprises an inorganic manganese salt.

11. The method according to claim 10, wherein the inorganic manganese salt comprises a mineral acid salt of manganese.

12. The method according to claim 1, wherein the nitrogen source derived from natural origin is selected from the group consisting of casamino acid, peptone, yeast extract and malt extract.

13. The method according to claim 1, which further comprises cultivating the medium at an acidic pH.

14. The method according to claim 1, which further comprises cultivating the medium at an initial temperature range of from about 25° to about 30° C., until the *Escherichia coli* growth measures about 1000 Klett units, followed by an increase in the cultivation temperature to a temperature of about 42° C.

15. The method according to claim 1, which further comprises cultivating the medium at an initial temperature of about 37° C., maintaining said temperature until the *Escherichia coli* growth measures about 500 Klett units, followed by a decrease in the cultivation temperature to a maintenance temperature range of from about 20° to 30° C.

* * * * *